US00PP34666P2

(12) United States Plant Patent
Lazzeri

(10) Patent No.: US PP34,666 P2
(45) Date of Patent: Oct. 18, 2022

(54) ***PELARGONIUM* PLANT NAMED 'LVPI1912'**

(50) Latin Name: *Pelargonium peltatum*
Varietal Denomination: LVPI1912

(71) Applicant: Carlo Lazzeri, Vacaria (BR)

(72) Inventor: Carlo Lazzeri, Vacaria (BR)

( * ) Notice: Subject to any disclaimer, the term of this patent is extended or adjusted under 35 U.S.C. 154(b) by 0 days.

(21) Appl. No.: 17/732,422

(22) Filed: Apr. 28, 2022

Related U.S. Application Data

(60) Provisional application No. 63/182,282, filed on Apr. 30, 2021.

(51) Int. Cl.
*A01H 5/02* (2018.01)
*A01H 6/42* (2018.01)

(52) U.S. Cl.
USPC ..... Plt./332

(58) Field of Classification Search
USPC ..... Plt./263.1, 324, 332
See application file for complete search history.

(56) References Cited

PUBLICATIONS

Ball Seed: Plant Information & more website, citation for Royal Dark Red Ivy Geranium. https://www.ballseed.com/webtrackplantinfo.aspx?phid=028401288004491. 2 pages. (Year: 2022).*

* cited by examiner

*Primary Examiner* — Karen M Redden
(74) *Attorney, Agent, or Firm* — C. Anne Whealy

(57) ABSTRACT

A new and distinct Ivy Geranium plant named 'LVPI1912', characterized by its upright to broadly spreading plant habit; moderately vigorous growth habit; freely branching habit; durable dark green-colored leaves; freely and early flowering habit; single dark red-colored flowers that are held above the foliar plane on moderately strong peduncles; and good garden performance.

2 Drawing Sheets

Figure 1:
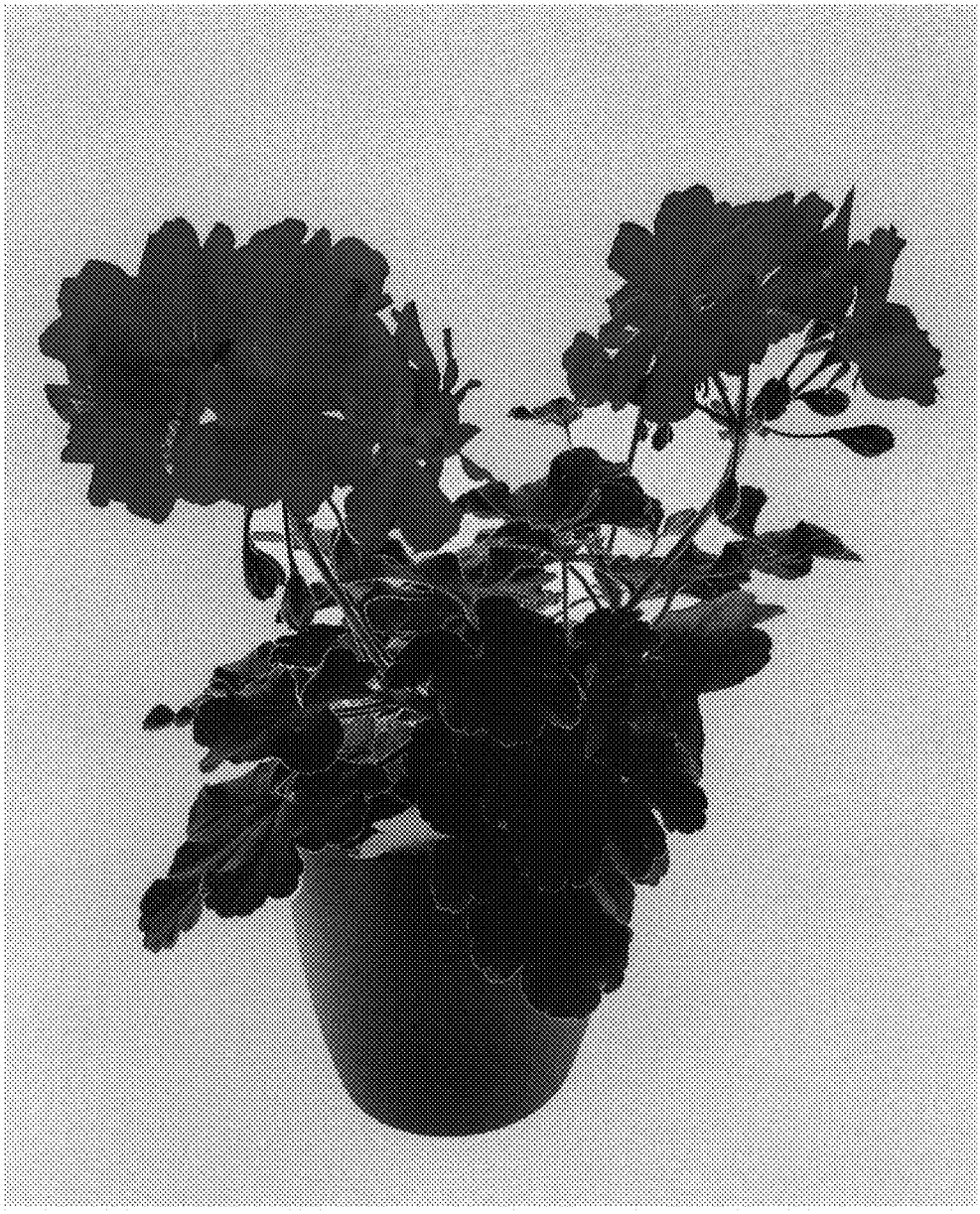

Botanical designation: *Pelargonium peltatum.*
Cultivar denomination: 'LVPI1912'.

CROSS-REFERENCED TO CLOSELY-RELATED APPLICATIONS

Title: Varieties of *Pelargonium* Plants
Inventor/Applicant: Carlo Lazzeri
Filed: Apr. 30, 2021
Ser. No.: 63/182,282
Inventor/Applicant hereby claims the benefit of this provisional U.S. Patent Application.

STATEMENT REGARDING PRIOR DISCLOSURES BY INVENTOR/APPLICANT

An European Plant Breeders' Rights application for the instant plant was filed by the Inventor/Applicant on Apr. 20, 2021, application number 2021/1083. Foreign priority is not claimed to this application.

The Inventor/Applicant assert that no publications nor advertisements relating to sales, offers for sale or public distribution occurred more than one year prior to the effective filing date of this application. Any information about the claimed plant would have been obtained from a direct or indirect disclosure from the Inventor/Applicant. Inventor/Applicant claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of Ivy Geranium plant, botanically known as *Pelargonium peltatum*, and hereinafter referred to by the name 'LVPI1912'.

The new Ivy Geranium plant is a product of a planned breeding program conducted by the Inventor in Vacaria, Brazil. The objective of the breeding program is to develop new strong and freely flowering Ivy Geranium plants with attractive flowers and good garden performance.

The new Ivy Geranium plant originated from a cross-pollination in January, 2018 in Vacaria, Brazil of *Pelargonium peltatum* 'Champion Red', not patented, as the female, or seed, parent with *Pelargonium peltatum* 'Calliope Dark Red', not patented, as the male, or pollen, parent. The new Ivy Geranium plant was discovered and selected by the Inventor as a single flowering plant from within the progeny of the stated cross-pollination grown in a controlled greenhouse environment in Vacaria, Brazil in January, 2019.

Asexual reproduction of the new Ivy Geranium plant by terminal stem cuttings in a controlled environment in Vacaria, Brazil since April, 2019 has shown that the unique features of this new Ivy Geranium plant are stable and reproduced true to type in successive generations.

SUMMARY OF THE INVENTION

Plants of the new Ivy Geranium have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'LVPI1912'. These characteristics in combination distinguish 'LVPI1912' as a new and distinct Ivy Geranium plant:

1. Upright to broadly spreading plant habit.

2. Moderately vigorous growth habit.
3. Freely branching habit.
4. Durable dark green-colored leaves.
5. Freely and early flowering habit.
6. Single dark red-colored flowers that are held above the foliar plane on moderately strong peduncles.
7. Good garden performance.

Plants of the new Ivy Geranium can be compared to plants of female parent, 'Champion Red'. In side-by-side comparisons, plants of the new Ivy Geranium differ primarily from plants of 'Champion Red' in the following characteristics:

1. Plants of the new Ivy Geranium are more uniform than plants of 'Champion Red'.
2. Flower petals of plants of the new Ivy Geranium are more symmetrical than flower petals of plants of 'Champion Red'.

Plants of the new Ivy Geranium can be compared to plants of male parent, 'Calliope Dark Red'. In side-by-side comparisons, plants of the new Ivy Geranium differ primarily from plants of 'Calliope Dark Red' in the following characteristics:

1. Plants of the new Ivy Geranium are not as vigorous as plants of 'Calliope Dark Red'.
2. Leaves of plants of the new Ivy Geranium are darker green in color than leaves of plants of 'Calliope Dark Red'.

Plants of the new Ivy Geranium can be compared to plants of the interspecific *Pelargonium* 'Cope Scarfir', disclosed in U.S. Plant Pat. No. 20,466. In side-by-side comparisons, plants of the new Ivy Geranium differ primarily from plants of 'Cope Scarfir' in the following characteristics:

1. Plants of the new Ivy Geranium are more compact than and not as vigorous as plants of 'Cope Scarfir'.
2. Plants of the new Ivy Geranium have dark red-colored flowers whereas plants of 'Cope Scarfir' have scarlet red-colored flowers.

BRIEF DESCRIPTION OF THE PHOTOGRAPHS

The accompanying colored photographs illustrate the overall appearance of the new Ivy Geranium plant showing the colors as true as it is reasonably possible to obtain in colored reproductions of this type. Colors in the photographs may differ slightly from the color values cited in the detailed botanical description which accurately describe the colors of the new Ivy Geranium plant.

The photograph on the first sheet (FIG. 1) is a side perspective view of a typical flowering plant of 'LVPI1912' grown in a container.

Figure 2:
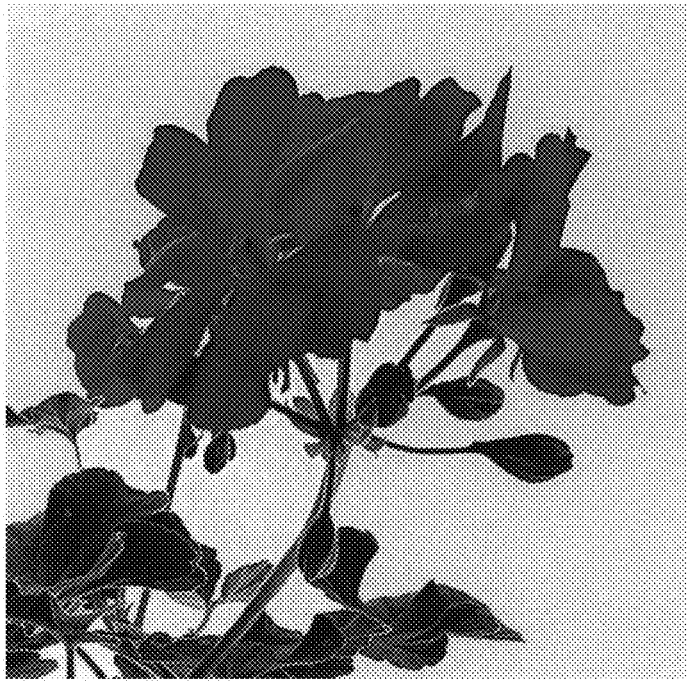

The photograph at the top of the second sheet (FIG. 2) is a close-up view of a typical flowering plant of 'LVPI1912'.

Figure 3:
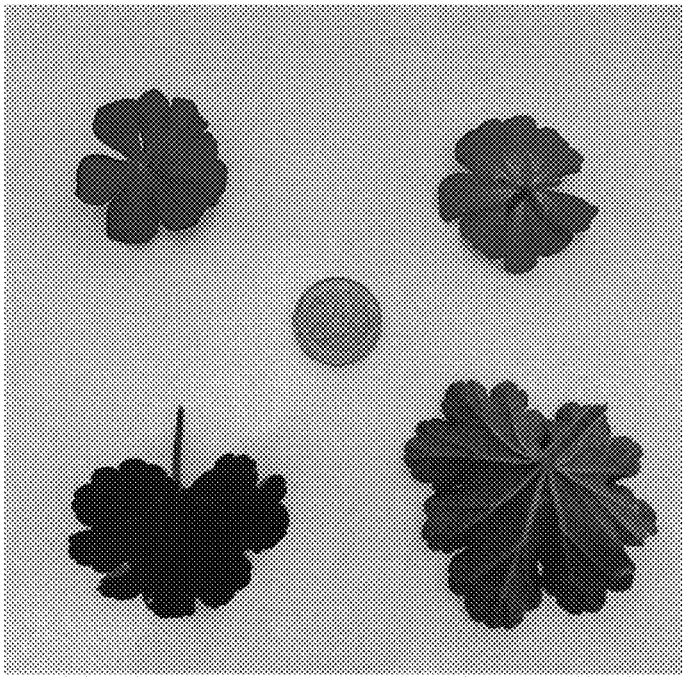

The photograph at the bottom of the second sheet (FIG. 3) are close-up views of the upper (left) and lower (right) surfaces of typical flowers and leaves of 'LVPI1912.'

DETAILED BOTANICAL DESCRIPTION

The aforementioned photograph and following observations, measurements and values describe plants grown in 12-cm containers during the summer in a polyethylene-covered greenhouse in Merano, Italy and under cultural practices typical of commercial Ivy Geranium production. During the production of the plants, day temperatures ranged from 15° C. to 28° C. and night temperatures ranged from 10° C. to 18° C. Plants were twelve weeks old when the photographs and detailed description were taken. In the detailed description, color references are made to The Royal Horticultural Society Colour Chart, 2015 Edition, except where general terms of ordinary dictionary significance are used.

Botanical classification: *Pelargonium peltatum* 'LVPI1912'.

Parentage:

*Female, or seed, parent.*—*Pelargonium peltatum* 'Champion Red', not patented.

*Male or pollen parent.*—*Pelargonium peltatum* 'Calliope Dark Red', not patented.

Propagation:

*Type.*—By vegetative terminal cuttings.

*Time to initiate roots, summer.*—About 12 days at temperatures about 25° C.

*Time to initiate roots, winter.*—About 16 days at temperatures about 14° C.

*Time to produce a rooted young plant, summer.*—About three weeks at temperatures about 25° C.

*Time to produce a rooted young plant, winter.*—About four weeks at temperatures about 14° C.

*Root description.*—Fine, fibrous; typically creamy white in color, actual color of the roots is dependent on substrate composition, water quality, fertilizers, substrate temperature and age of roots.

*Rooting habit.*—Freely branching; medium density.

Plant description:

*Plant and growth habit.*—Upright to broadly spreading plant habit; flattened globular in overall shape; densely foliated; moderately vigorous growth habit and moderate growth rate; freely basal branching habit with about three primary lateral branches with numerous secondary lateral branches developing per plant; pinching is typically not required.

*Plant height, to top of foliar plane.*—About 15.3 cm.

*Plant height, to top of floral plane.*—About 19.8 cm.

*Plant width.*—About 27.1 cm.

*Lateral branches.*—Length: About 6 cm. Diameter: About 6 mm. Internode length: About 2.1 cm. Strength: Moderately strong. Aspect: About 30° to 60° from vertical. Texture and luster: Densely pubescent; slightly glossy. Color, developing: Close to 144A. Color, developed: Upper surface, close to 143A and lower surface, close to 143B; at the internodes, close to 143A.

Leaf description:

*Arrangement.*—Opposite and alternate; simple.

*Length.*—About 6.7 cm.

*Width.*—About 7.6 cm.

*Shape.*—Reniform.

*Apex.*—Rounded.

*Base.*—Hastate, lobes free.

*Margin.*—Coarsely crenate with about nine lobes; sinuses divergent and relatively shallow.

*Venation pattern.*—Palmate.

*Texture and luster, upper surface.*—Densely pubescent; velvety; matte.

*Texture and luster, lower surface.*—Densely pubescent; velvety; slightly glossy.

*Color.*—Developing leaves, upper surface: Close to 137A. Developing leaves, lower surface: Close to 138B. Fully expanded leaves, upper surface: Close to NN137A; towards the base, close to NN137C; venation, close to 143B; no discernible zonation pattern. Fully expanded leaves, lower surface: Close to 147B; venation, close to 146D.

*Petioles*.—Length: About 5.8 cm. Diameter: About 2.5 mm. Strength: Moderately strong. Texture and luster, upper and lower surfaces: Densely pubescent; moderately glossy. Color, upper surface: Close to 144A. Color, lower surface: Close to 143B.

*Stipules*.—Quantity and arrangement: Two, opposite. Length: About 1.3 cm. Width: About 7.5 mm. Shape: Ovate. Apex: Acute to apiculate. Base: Broadly cuneate. Texture, upper and lower surfaces: Densely pubescent. Color, upper surface: Close to 143B. Color, lower surface: Close to 143C.

Flower description:

*Flower arrangement and flowering habit*.—Single-type rotate flowers arranged in hemispherical umbels arising from apical leaf axils; umbels displayed above the foliar plane on moderately strong peduncles; flowers face upright to outwardly depending on the position in the umbel; freely flowering habit with about eleven flowers developing per umbel and numerous umbels developing per plant during the flowering season.

*Fragrance*.—None detected.

*Flowering season*.—Early flowering habit; plants begin flowering about 30 days after planting; in the garden, flowering begins in the spring and continues until frost in the autumn.

*Flower longevity*.—Individual flowers last about one week on the plant; flowers persistent.

*Umbel height*.—About 5.9 cm.

*Umbel diameter*.—About 9 cm.

*Flower diameter*.—About 4.3 cm by 4.7 cm.

*Flower depth* (*height*).—About 2.2 cm.

*Flower buds*.—Length: About 1.1 cm. Diameter: About 7 mm. Shape: Obovate. Texture and luster: Moderately to densely pubescent; moderately glossy. Color: Developing sepals, close to 143A; developing petals, close to a blend of 53A and 59B.

*Petals*.—Quantity per flower: Typically seven, arranged in one to two whorls. Length, upper petals: About 2.8 cm. Length, lower petals: About 2.6 cm. Width, upper petals: About 1.5 cm. Width, lower petals: About 1.8 cm. Shape, all petals: Obovate. Apex, all petals: Rounded. Base, all petals: Acuminate. Margin, all petals: Entire; slightly undulate. Texture and luster, all petals, upper surface: Smooth, glabrous; velvety; matte. Texture and luster, all petals, lower surface: Smooth, glabrous; slightly velvety; matte. Color: When opening, upper petals, upper surface: Close to 53A; towards the base, close to 53C. When opening, lower petals, upper surface: Close to 53A. When opening, upper petals, lower surface: Close to 53C; towards the base, close to 60B. When opening, lower petals, lower surface: Close to 53C. Fully opened, upper petals, upper surface: Close to a blend of N45A and 53A; towards the base, close to 53C; venation, close to 60A; color does not change with subsequent development. Fully opened, lower petals, upper surface: Close to 53A; towards the base, close to N45B to N45C; venation, close to 60A; color does not change with subsequent development. Fully opened, upper petals, lower surface: Close to 53C; towards the base, close to 54B; venation, close to 187C; color does not change with subsequent development. Fully opened, lower petals, lower surface: Close to 58B; venation, close to 187C; color does not change with subsequent development.

*Petaloids*.—To date, petaloid development has not been observed on plants of the new Ivy Geranium.

*Sepals*.—Quantity per flower: Five arranged in a single whorl. Length: About 1.1 cm. Width: About 3 mm. Shape: Narrowly oblong. Apex: Short apiculate. Base: Cuneate. Margin: Entire. Texture and luster, upper surface: Smooth, glabrous; slightly glossy. Texture and luster, lower surface: Moderately to densely pubescent; slightly glossy. Color: When opening, upper surface: Close to 144A. When opening, lower surface: Close to a blend of 143A and 144A. Fully opened, upper surface: Close to 144A; color becoming closer to 176B with subsequent development. Fully opened, lower surface: Close to a blend of 143B and 144A; towards the base, tinged with close to 176B to 176C.

*Peduncles* (*umbel stems*).—Length: About 7.3 cm. Diameter: About 2.75 mm. Strength: Moderately strong; flexible. Aspect: About 22.5° from lateral branch axis. Texture and luster: Densely pubescent; slightly glossy. Color: Close to 143C.

*Pedicels* (*individual flower stems*).—Length: About 2.6 cm. Diameter: About 1.25 mm. Strength: Moderately strong; flexible. Aspect: Upright to about 90° from peduncle axis depending on position in the umbel. Texture and luster: Densely pubescent; glossy. Color: Close to a blend of 183A and N186C; towards the base, close to 148A.

*Floral bracts*.—Quantity and arrangement: About seven at the top of the peduncle. Length: About 7 mm. Width: About 2.5 mm. Shape: Obovate to short oblong. Apex: Abruptly acute. Base: Broadly cuneate. Texture, upper and lower surfaces: Densely pubescent. Color, upper and lower surfaces: Close to 143A to 143B.

*Reproductive organs*.—Androecium: Stamen quantity per flower: About ten. Filament length: About 5 mm. Filament color: Close to 67B; towards the base, close to NN155D. Anther size: About 1 mm by 2 mm. Anther shape: Oblong. Anther color: Close to 59A. Pollen amount: Abundant. Pollen color: Close to 34C. Gynoecium: Pistil quantity per flower: One. Pistil length: About 3.5 mm. Stigma diameter: About 4 mm. Stigma shape: Five-parted. Stigma color: Close to 59C. Style length: About 2 mm. Style color: Close to 59D. Ovary color: Close to 147C. Seeds and fruits: To date, seed and fruit development have not been observed on plants of the new Ivy Geranium.

Pathogen & pest resistance: To date, plants of the new Ivy Geranium have not been observed to be resistant to pathogens and pests common to Ivy Geraniums.

Garden performance & temperature tolerance: Plants of the new Ivy Geranium have been observed to have good garden performance, to tolerate temperatures ranging from about 5° C. to about 40° C. and to be suitable for USDA Hardiness Zones 10 to 13.

It is claimed:

1. A new and distinct Ivy Geranium plant named 'LVPI1912' as illustrated and described.

* * * * *